United States Patent
Masuda

(10) Patent No.: US 10,196,409 B2
(45) Date of Patent: Feb. 5, 2019

(54) ORGANOSILICON COMPOUND AND CURABLE COMPOSITION

(71) Applicant: SHIN-ETSU CHEMICAL CO., LTD., Tokyo (JP)

(72) Inventor: Kohei Masuda, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 15/420,400

(22) Filed: Jan. 31, 2017

(65) Prior Publication Data

US 2017/0240573 A1    Aug. 24, 2017

(30) Foreign Application Priority Data

Feb. 23, 2016   (JP) ................... 2016-031818

(51) Int. Cl.
| | | |
|---|---|---|
| C07F 7/21 | (2006.01) | |
| C08F 120/36 | (2006.01) | |
| C09D 4/00 | (2006.01) | |
| C08F 30/08 | (2006.01) | |
| C08F 220/12 | (2006.01) | |
| C08F 230/08 | (2006.01) | |

(52) U.S. Cl.
CPC .............. *C07F 7/21* (2013.01); *C08F 30/08* (2013.01); *C08F 120/36* (2013.01); *C08F 220/12* (2013.01); *C08F 230/08* (2013.01); *C09D 4/00* (2013.01)

(58) Field of Classification Search
CPC ........ C07F 7/21; C08F 230/08; C08F 220/12; C08F 120/36; C08F 30/08; C09D 4/00
See application file for complete search history.

(56) References Cited

U.S. PATENT DOCUMENTS

| 6,258,347 B1 * | 7/2001 | Sakuta ................... A61K 8/585 424/401 |
| 8,314,264 B2 | 11/2012 | Tsuchida et al. |
| 9,303,180 B2 | 4/2016 | Yamada et al. |
| 2010/0210862 A1 * | 8/2010 | Tsuchida ............... C07F 7/1836 556/421 |

FOREIGN PATENT DOCUMENTS

| EP | 475437 A1 * | 3/1992 | ............... C07F 7/21 |
| EP | 2 801 596 A1 | 11/2014 | |
| JP | 08-104846 * | 4/1996 | ........... C09D 201/02 |
| JP | 2010-189294 A | 9/2010 | |
| JP | 2013-035274 A | 2/2013 | |
| JP | 2014-218593 A | 11/2014 | |

OTHER PUBLICATIONS

Kinoshita et al., "Selective Synthesis of cis-trans-cis Cyclic Tetrasiloxanes and the Formation of Their Two-Dimensional Layered Aggregates", Journal of the American Chemical Society, vol. 137, 2015, pp. 5061-5065.

* cited by examiner

*Primary Examiner* — Jessica M Roswell

(74) *Attorney, Agent, or Firm* — Birch, Stewart, Kolasch & Birch, LLP

(57) ABSTRACT

A cyclic organosilicon compound having a (meth)acrylic group and a urea structure on a silicon atom cures into a product having improved flexibility, surface hardness, and evaporation amenability.

18 Claims, 4 Drawing Sheets

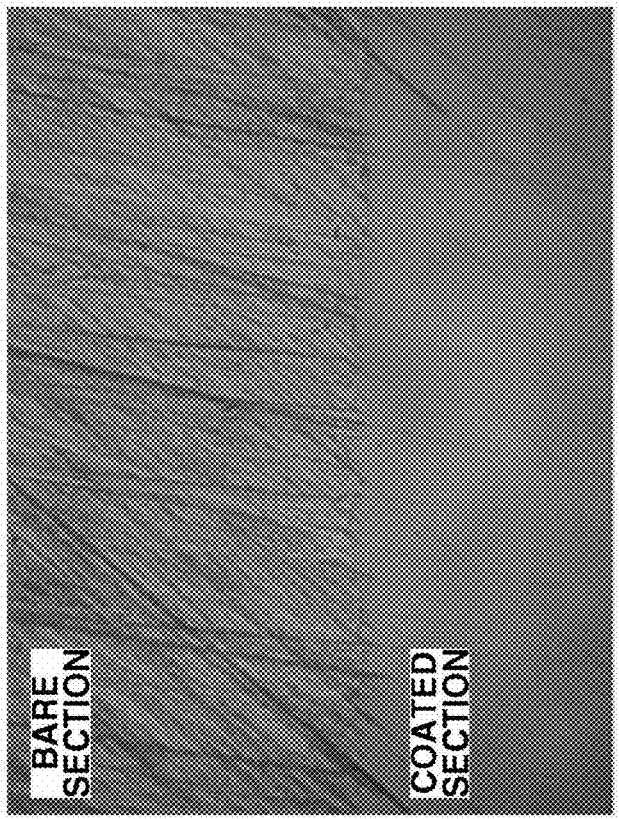

# ORGANOSILICON COMPOUND AND CURABLE COMPOSITION

CROSS-REFERENCE TO RELATED APPLICATION

This non-provisional application claims priority under 35 U.S.C. § 119(a) on Patent Application No. 2016-031818 filed in Japan on Feb. 23, 2016, the entire contents of which are hereby incorporated by reference.

TECHNICAL FIELD

This invention relates to an organosilicon compound and a curable composition comprising the same. More particularly, it relates to a cyclic organosilicon compound having a multi-functional (meth)acrylic group and a urea structure and an actinic radiation-curable composition comprising the same.

BACKGROUND ART

Polymerizable vinyl monomers are known in the art as photo-reactive compounds. Photo-cured products of polymerizable vinyl monomers, however, lack weather resistance and chemical properties since they consist solely of organics. Many attempts were made to convert photo-reactive organosilicon compounds into organic-inorganic hybrid compounds which can overcome the problems.

For example, Patent Document 1 discloses a method for polycondensation of an acrylic functional silane to form a polyhedral oligomeric silsesquioxane (known as POSS) which meets both photo-reactivity and receptivity to inorganic evaporation (e.g., CVD). The inventor's experimentation reveals that the POSS having a multi-functional acrylic moiety exhibits insufficient flexibility.

Various attempts were made to impart flexibility to photo-reactive organosilicon compounds. For example, Patent Document 2 proposes a long-chain linker between an acrylic moiety and a silicon atom and Patent Document 3 proposes to introduce a urea structure into such a linker. However, these techniques have the problem that the cured products have insufficient surface hardness and less amenability to inorganic evaporation as long as the inventor studied.

Recently, attention is paid to the precise control of polycondensation of organosilicon compounds. For example, Non-Patent Document 1 reports highly selective synthesis of a silicon compound by hydrolytic condensation of an amino-functional organosilicon compound with a superstrong acid. Although Non-Patent Document 1 aims at structural analysis of the organosilicon compound and refers to the formation of a regular structure two-dimensional film, it refers nowhere to the industrial applicability of the two-dimensional film or further molecular transformation of the compound into a useful compound. Since the point of view is different from Patent Document 3, it is not believed that the organosilicon compound can be readily converted into a useful compound by similar urea type molecular transformation.

CITATION LIST

Patent Document 1: JP-A 2013-35274
Patent Document 2: JP-A 2014-218593 (U.S. Pat. No. 9,303,180, EP 2801596)
Patent Document 3: JP-A 2010-189294 (U.S. Pat. No. 8,314,264)
Non-Patent Document 1: J. Am. Chem. Soc., 2015, 137, 5061-5065

SUMMARY OF INVENTION

An object of the invention is to provide an organosilicon compound which cures into an organic-inorganic hybrid cured product having improved flexibility, surface hardness, and evaporation amenability and an actinic radiation-curable composition comprising the compound.

The inventor has found that a unique cyclic organosilicon compound having a (meth)acrylic group and a urea structure on a silicon atom affords a photo-cured product having significantly improved flexibility, surface hardness, and evaporation amenability, in contrast to analogous silicon compounds.

In one aspect, the invention provides an organosilicon compound having the general formula (1):

$$\left[\begin{array}{c} R^1 \\ | \\ -\!\!\!\!-\!\!\text{Si}\!-\!\!\text{O}\!\!-\!\!\!\!\!- \\ | \\ Y^1\!\!-\!\!\text{N}\!\!-\!\!\underset{\underset{H}{|}}{\overset{\underset{|}{\parallel}}{C}}\!\!-\!\!\underset{H}{\overset{|}{N}}\!\!-\!\!Y^2\!\!-\!\!O\!\!-\!\!\overset{O}{\overset{\parallel}{C}}\!\!-\!\!\overset{CH_2}{\overset{\parallel}{C}}\!\!-\!\!R^2 \end{array}\right]_4 \tag{1}$$

wherein $R^1$ is a $C_1$-$C_6$ alkyl group, $R^2$ is hydrogen or methyl, and $Y^1$ and $Y^2$ are each independently a $C_1$-$C_{10}$ linear alkylene group. Preferably, $R^1$ is a $C_1$-$C_3$ alkyl group, $R^2$ is hydrogen, and $Y^1$ and $Y^2$ are each independently a $C_1$-$C_5$ linear alkylene group.

In another aspect, the invention provides an actinic radiation-curable composition comprising the organosilicon compound defined above, preferably in an amount of at least 10% by weight.

Advantageous Effects of Invention

As defined above, the invention provides a photo-curable organosilicon compound which affords a cured product having flexibility, surface hardness, and evaporation amenability, and a curable composition comprising the same. Since the inventive organosilicon compound cures into a product having improved flexibility and surface hardness, it is advantageously used where there exists a need to further improve the properties of prior art organosilicon compounds including crack resistance and dimensional stability. Since a cured product of the organosilicon compound meets both flexibility and surface hardness, the organosilicon compound is advantageously used as a hard coat agent, primer for CVD, electronic component encapsulant, and epoxy resin curing agent.

BRIEF DESCRIPTION OF DRAWING

FIG. 4 is a photograph of the cured product-coated section and bare section of the sheet sample in Example 3-1 for comparison of mar resistance.

DESCRIPTION OF PREFERRED EMBODIMENTS

Figure 1:
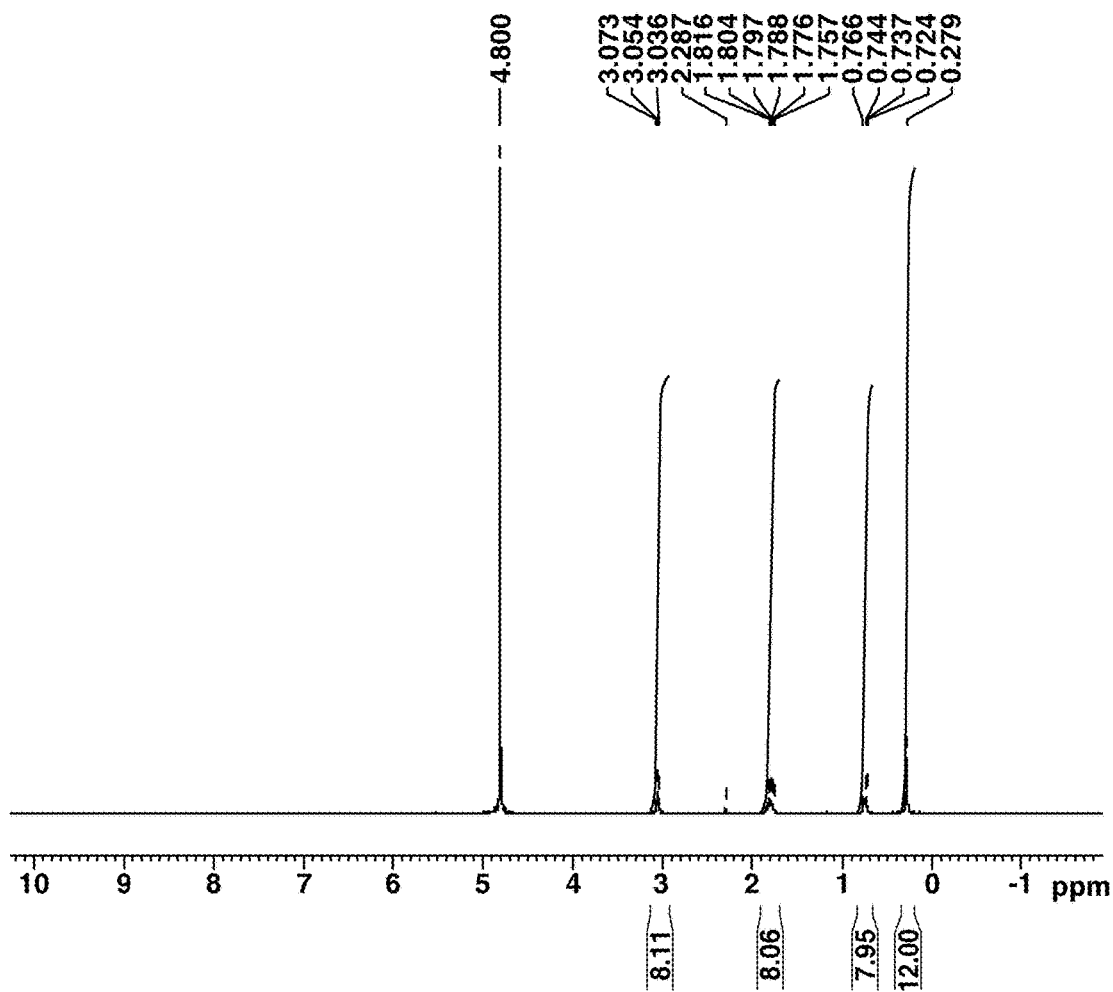
FIG. 1 is a diagram of $^1$H NMR spectrum of the compound obtained in Synthesis Example 1.

As used herein, the notation (Cn-Cm) means a group containing from n to m carbon atoms per group. Also, the term "(meth)acrylic" is intended to mean acrylic or methacrylic.

The organosilicon compound of the invention is a single tetramer having the following formula (1).

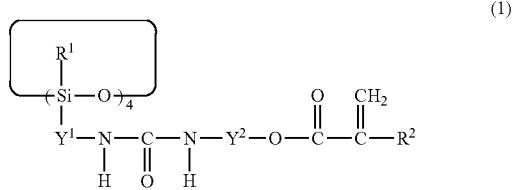

Herein $R^1$ is a $C_1$-$C_6$ alkyl group, $R^2$ is hydrogen or methyl, and $Y^1$ and $Y^2$ are each independently a $C_1$-$C_{10}$ linear alkylene group.

The $C_1$-$C_6$ alkyl group may be linear, cyclic or branched, examples of which include methyl, ethyl, n-propyl, i-propyl, n-butyl, s-butyl, t-butyl, n-pentyl, n-hexyl, cyclopropyl, cyclobutyl, cyclopentyl, and cyclohexyl. Examples of the $C_1$-$C_{10}$ linear alkylene group include methylene, ethylene, trimethylene, tetramethylene, pentamethylene, hexamethylene (or hexylene), heptamethylene, octamethylene (or octylene), nonamethylene, and decamethylene, though not limited thereto.

Of these groups, $R^1$ is preferably a linear alkyl group, more preferably methyl, ethyl, n-propyl, n-butyl, n-pentyl, or n-hexyl, with methyl being most preferred. $R^2$ is preferably hydrogen from the aspect of synthetic chemistry. $Y^1$ is preferably a $C_1$-$C_8$ linear alkylene group, more preferably methylene, ethylene, trimethylene, hexylene, or octylene, with trimethylene being most preferred from the aspect of synthetic chemistry. $Y^2$ is preferably a $C_1$-$C_8$ linear alkylene group, more preferably methylene, ethylene, trimethylene, hexylene, or octylene, with ethylene being most preferred from the aspect of synthetic chemistry. A long-chain group like octylene may be preferred as $Y^2$ when it is desired to impart flexing property to the organosilicon compound.

The organosilicon compound is a cyclic tetramer. For the cyclic tetramer of siloxane, specific structural isomers exist because silicon-bonded organic groups cannot rotate or invert. With regard to the same substituents $R^1$, according to the nomenclature rules, the structure wherein two adjacent $R^1$ groups are on the same side of the ring is referred to as "cis", and the structure wherein they are on opposite sides is referred to as "trans". In the case of a cyclic tetramer, once consecutive three structures among adjacent structures are appointed, the remaining one is inevitably determined. The molecular structure can be expressed as cis-cis-cis, cis-trans-cis or the like. Since the notation of the structure is determined by selecting from cis and trans (i.e., two choices) three times, formally there are present $2^3$ (=8) combinations. However, since all structures have an image plane in the molecule, they are classified to 4 types of structural isomers according to the group theory. Although the organosilane compound (or organosilicon compound) may be any of these four types of isomers or a mixture thereof, the cis-trans-cis isomer is preferred in that a regular structure is likely to form therefrom.

The method for synthesizing the organosilane compound of formula (1) is not particularly limited. The compound may be synthesized by any well-known techniques. A method including steps (A) and (B) to be described below is preferred from the industrial aspect because the relevant compound can be readily prepared at a high selectivity in high yields.

(A) Synthesis of Cyclotetrasiloxane

A cyclotetrasiloxane can be synthesized according to the method disclosed in Non-Patent Document 1. This method is characterized by hydrolytic condensation of an amino-containing organosilicon compound with the aid of a superstrong acid, for thereby forming a single stereoisomer and tetramer in high yields. When this method is used, the organosilicon compound of formula (1) is also a single stereoisomer and cyclic tetramer.

Suitable amino-containing organosilicon compounds used in this method include 3-aminopropylmethyldimethoxysilane, 3-aminopropylmethyldiethoxysilane, N-(2-aminoethyl)-3-aminopropylmethyldimethoxysilane, and N-(2-aminoethyl)-3-aminopropylmethyldiethoxysilane. Of these, 3-aminopropylmethyldiethoxysilane is preferred for ease of handling during synthesis operation. Commercially, 3-aminopropylmethyldiethoxysilane is available under the trade name, for example, of KBE-902 from Shin-Etsu Chemical Co., Ltd.

Although only compounds having a linking chain of three carbon atoms between the silicon atom and the amino-functional moiety are exemplified, compounds having a linking chain of 1 to 10 carbon atoms are suitably used as described above for $Y^1$. Similarly, although only compounds having methyl as the silicon-bonded carbon group are exemplified, compounds having a group of 1 to 6 carbon atoms are suitably used as described above for $R^1$.

Examples of the superstrong acid include sulfonic acids such as trifluoromethanesulfonic acid, methanesulfonic acid, p-toluenesulfonic acid, and benzenesulfonic acid; fluorocarboxylic acids such as trifluoroacetic acid, difluoroacetic acid, pentafluoropropionic acid, and pentafluorobenzoic acid; and protonic acids which are ate complexes of Group 13 and Group 15 elements such as hexafluoroantimonate, tetrafluoroborate, and tetrachloroaluminate, which may be used alone or in admixture of two or more. The superstrong acid used herein should preferably contain trifluoromethanesulfonic acid.

(B) Addition of (Meth)Acrylic Isocyanate

Step (B) is addition of the amino group of the amino-containing cyclotetrasiloxane synthesized in step (A) to a (meth)acrylic isocyanate.

Suitable (meth)acrylic isocyanates used in this reaction include 2-isocyanatoethyl acrylate and 2-isocyanatoethyl methacrylate, with 2-isocyanatoethyl acrylate being preferred from the aspects of availability and reactivity. Commercially, 2-isocyanatoethyl acrylate is available under the trade name, for example, of Karenz AOI from Showa Denko K.K.

Although only compounds having a linking chain of two carbon atoms between the (meth)acryloyloxy group and the isocyanato group are exemplified, compounds having a linking chain of 1 to 10 carbon atoms are suitably used as described above for $Y^2$.

Sometimes, the amino-containing cyclotetrasiloxane obtained in step (A) has formed a salt with the superstrong acid used for hydrolytic condensation. If so, its nucleophilicity to isocyanate is low. In such a case, the reaction is preferably promoted by the co-presence of a base. The base may be either organic or inorganic.

Examples of the organic base include organic compounds of Group 15 elements such as triethylamine, pyridine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), bissilylated acetamide (BSA), and triphenylphosphine. Examples of the inorganic base include alkaline and alkaline earth metal salts such as sodium hydroxide, sodium carbonate, sodium hydrogencarbonate, calcium hydroxide, and lithium diisopropylamide (LDA). Notably some types of bases have nucleophilicity to the isocyanate. If so, the nucleophilic reaction between the base and the isocyanate may become competitive with the nucleophilic reaction between the amino group and the isocyanate. In such probability, a non-nucleophilic base is preferably selected.

The reaction in step (B) may be performed in an organic solvent. The organic solvent is not particularly limited as long as it does not adversely affect the reaction. For this reaction, aprotic polar solvents such as tetrahydrofuran (THF), N,N-dimethylformamide (DMF), N,N-dimethylacetamide, and acetonitrile are suitable from the aspects of solubility and reactivity. After the reaction, the organosilicon compound is readily recovered by removing the solvent.

Besides the aforementioned method including steps (A) and (B), the organosilicon compound may also be prepared by simple hydrolytic condensation of an alkoxysilane and subsequent separation step such as reprecipitation, recrystallization, sublimation, distillation, or size-exclusion gel filtration of the resulting polymer mixture to increase the purity of the desired tetramer.

The final purity of the organosilicon compound is preferably at least 50 mol %, more preferably at least 70 mol %, and even more preferably at least 90 mol %. Although the upper limit of the purity is not critical, a higher purity is recommended for the following reason. When a curable composition is prepared using the organosilicon compound as will be described below, the composition should preferably contain at least 10% by weight of the organosilicon compound. Using the organosilicon compound of higher purity, a satisfactory curable composition is readily obtained.

Another embodiment of the invention is an actinic radiation-curable composition comprising the organosilicon compound defined above, preferably in an amount of at least 10% by weight.

Examples of the actinic radiation used herein include light, electron beam (EB), and radiation. Examples of the energy source or curing system include UV from germicidal lamps, UV-emitting fluorescent lamps, carbon arc lamps, xenon lamps, high pressure mercury lamps for copiers, medium and high pressure mercury lamps, extra-high pressure mercury lamps, electrodeless lamps, metal halide lamps, and natural light, and EBs from scanning and curtain-type EB accelerators, with UV being preferred.

In addition to the organosilicon compound, the curable composition may further comprise a polymerizable vinyl monomer, inorganic oxide filler, photoinitiator, solvent and the like.

The polymerizable vinyl monomer used herein is not particularly limited. Examples include monoesters such as methyl methacrylate (abbr. MMA), methyl acrylate (abbr. MA), ethyl methacrylate, ethyl acrylate, hydroxyethyl acrylate (abbr. HEA), hydroxyethyl methacrylate (abbr. HEMA), hydroxypropyl acrylate, 4-hydroxybutyl acrylate, isobutyl acrylate, t-butyl acrylate, n-octyl acrylate, isooctyl acrylate, isononyl acrylate, lauryl acrylate, stearyl acrylate, isostearyl acrylate, isonorbornyl acrylate, tetrahydrofurfuryl acrylate, methoxyethyl acrylate, methoxypolyethylene glycol acrylate, 2-methyl-2-ethyl-1,3-dioxolan-4-yl acrylate, [cyclohexanespiro-2-(1,3-dioxolan-4-yl)]methyl acrylate, and (3-ethyloxetan-3-yl)methyl acrylate;

diesters such as ethylene glycol diacrylate, propylene glycol diacrylate, butanediol diacrylate, pentanediol diacrylate, hexanediol diacrylate, heptanediol diacrylate, octanediol diacrylate, nonanediol diacrylate, decanediol diacrylate, glycerol 1,2-diacrylate, glycerol 1,3-diacrylate, pentaerythritol diacrylate, 2-hydroxy-3-acryloyloxypropyl methacrylate, tricyclodecane dimethanol diacrylate, dipropylene glycol diacrylate, and tripropylene glycol diacrylate;

polyfunctional esters such as glycerol triacrylate, trimethylolpropane triacrylate, pentaerythritol triacrylate, dipentaerythrytol triacrylate, ethoxylated isocyanuric acid triacrylate, ethoxylated glycerol triacrylate, ethoxylated trimethylolpropane triacrylate, pentaerythritol tetraacrylate, dipentaerythritol hexaacrylate, ditrimethylolpropane tetraacrylate, ethoxylated pentaerythritol tetraacrylate, trimethylolpropane trimethacrylate, and trispentaerythritol octaacrylate; and polyfunctional esters which are basic hydrolytic condensates of (meth)acryloyloxyalkylenealkoxysilanes such as acryloyloxymethyltrimethoxysilane, acryloyloxymethyldimethoxymethylsilane, acryloyloxymethylmethoxydimethylsilane, methacryloyloxymethyltrimethoxymethylsilane, methacryloyloxymethyldimethoxymethylsilane, methacryloyloxymethylmethoxydimethylsilane, 2-acryloyloxyethyltrimethoxysilane, 2-acryloyloxyethyldimethoxymethylsilane, 2-acryloyloxyethylmethoxydimethylsilane, 2-methacryloyloxyethyltrimethoxysilane, 2-methacryloyloxyethyldimethoxymethylsilane, 2-methacryloyloxyethylmethoxydimethylsilane, 3-acryloyloxypropyltrimethoxysilane, 3-acryloyloxypropyldimethoxymethylsilane, 3-acryloyloxypropylmethoxydimethylsilane, 3-methacryloyloxypropyltrimethoxysilane, 3-methacryloyloxypropyldimethoxymethylsilane, 3-methacryloyloxypropylmethoxydimethylsilane, 8-acryloyloxyoctyltrimethoxysilane, 8-methacryloyloxyoctyltrimethoxysilane, acryloyloxymethyltriethoxysilane, acryloyloxymethyldiethoxymethylsilane, acryloyloxymethylethylethoxydimethylsilane, methacryloyloxymethyltriethoxysilane, methacryloyloxymethyldiethoxymethylsilane, methacryloyloxymethylethoxydimethylsilane, 2-acryloyloxyethyltriethoxysilane, 2-acryloyloxyethyldiethoxymethylsilane, 2-acryloyloxyethylethoxydimethylsilane, 2-methacryloyloxyethyltriethoxysilane, 2-methacryloyloxyethyldiethoxymethylsilane, 2-methacryloyloxyethylethoxydimethylsilane, 3-acryloyloxypropyltriethoxysilane, 3-acryloyloxypropyldiethoxymethylsilane, 3-acryloyloxypropylethoxydimethylsilane, 3-methacryloyloxypropyltriethoxysilane, 3-methacryloyloxypropyldiethoxymethylsilane, 3-methacryloyloxypropylethoxydimethylsilane, 8-acryloyloxyoctyltriethoxysilane, and 8-methacryloyloxyoctyltriethoxysilane, which may be used alone or in admixture of two or more.

When used, the content of the polymerizable vinyl monomer is preferably 10 to 90% by weight, more preferably 20 to 90% by weight, based on the curable composition, though not limited thereto.

The inorganic oxide filler is not particularly limited. Examples include inorganic oxide fine particles such as silicon oxide, zinc oxide, titanium oxide, cerium oxide, and aluminum oxide, which may be used alone or in admixture of two or more. When used, the content of the inorganic oxide filler is preferably 1 to 30% by weight, more preferably 5 to 20% by weight, based on the curable composition, though not limited thereto.

The photoinitiator is not particularly limited. Examples include alkylphenones such as 2,2-dimethoxy-1,2-diphenylethan-1-one, 1-hydroxycyclohexyl phenyl ketone, 2-hydroxy-2-methyl-1-phenylpropan-1-one, 1-[4-(2-hydroxyethoxy)-phenyl]-2-hydroxy-2-methylpropan-1-one, and methyl phenylglyoxylate; aminoalkylphenones such as 2-methyl-1-(4-methylthiophenyl)-2-morpholinopropan-1-one, 2-benzyl-2-dimethylamino-1-(4-morpholinophenyl)-butanone-1, and 2-(dimethylamino)-2-[(4-methylphenyl) methyl]-1-[4-(4-morpholinyl)phenyl]-1-butanone; and phosphine oxides such as 2,4,6-trimethylbenzoyldiphenylphosphine oxide and bis(2,4,6-trimethylbenzoyl)phenylphosphine oxide, which may be used alone or in admixture of two or more. When used, the content of the photoinitiator is preferably 0.1 to 20% by weight, more preferably 1 to 10% by weight, based on the curable composition, though not limited thereto.

The solvent is not particularly limited. Examples include $C_5$-$C_{30}$ hydrocarbon compounds such as pentane, hexane, heptane, octane, nonane, decane, undecane, dodecane, tridecane, tetradecane, pentadecane, hexadecane, heptadecane, octadecane, nonadecane, icosane, docosane, tricosane, tetracosane, pentacosane, hexacosane, heptacosane, octacosane, nonacosane, triacontane, benzene, toluene, o-xylene, m-xylene, p-xylene, petroleum ether (or a mixture of the foregoing), kerosene, ligroin, and Nujol; mono- and polyhydric alcohols such as methanol, ethanol, 1-propanol 2-propanol, cyclopentanol, ethylene glycol, propylene glycol, β-thiodiglycol, butylene glycol, and glycerol; ether compounds such as diethyl ether, dipropyl ether, cyclopentyl methyl ether, ethylene glycol dimethyl ether, diethylene glycol dimethyl ether, triethylene glycol dimethyl ether, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, butylene glycol monomethyl ether, butylene glycol monoethyl ether, butylene glycol monopropyl ether, and butylene glycol monobutyl ether; ester compounds such as methyl formate, ethyl formate, propyl formate, butyl formate, methyl acetate, ethyl acetate, propyl acetate, butyl acetate, methyl propionate, ethyl propionate, propyl propionate, butyl propionate, methyl butyrate, ethyl butyrate, propyl butyrate, butyl butyrate, methyl benzoate, ethyl benzoate, propyl benzoate, butyl benzoate, dimethyl oxalate, diethyl oxalate, dipropyl oxalate, dibutyl oxalate, dimethyl malonate, diethyl malonate, dipropyl malonate, dibutyl malonate, ethylene glycol diformate, ethylene glycol diacetate, ethylene glycol dipropionate, ethylene glycol dibutyrate, propylene glycol diacetate, propylene glycol dipropionate, propylene glycol dibutyrate, ethylene glycol methyl ether acetate, propylene glycol methyl ether acetate, butylene glycol monomethyl ether acetate, ethylene glycol ethyl, ether acetate, propylene glycol ethyl ether acetate, and butylene glycol monoethyl ether acetate; ketone compounds such as acetone, diacetone alcohol, diethyl ketone, methyl ethyl ketone, methyl isobutyl ketone, methyl n-butyl ketone, dibutyl ketone, cyclopentanone, cyclohexanone, cycloheptanone, and cyclooctanone; amide compounds such as dimethylformamide, dimethylacetamide, tetraacetylethylenediamide, tetraacetylhexamethylenetetramide, and N,N-dimethylhexamethylenediamine diacetate; and water, which may be used alone or in admixture of two or more. When used, the content of the solvent is preferably 10 to 90% by weight, more preferably 20 to 60% by weight, based on the curable composition, though not limited thereto.

The curable composition can be prepared by mixing the organosilane compound of formula (1) and the above optional components in any desired order.

The curable composition may have a solids concentration of about 1 to about 50% by weight, preferably 5 to 30% by weight, and more preferably 10 to 30% by weight. The term "solids" is used to encompass all components excluding the solvent.

The curable composition may be coated to substrates before it is cured into a cured product (cured coating) by exposing to actinic radiation, typically UV. The dose of irradiation energy may be properly selected. Irradiation may be combined with heating. The substrate used herein is not particularly limited and includes molded resins, ceramics, and glass.

Any suitable coating technique may be selected from various well-known coating techniques such as brush coating, spraying, dipping, flow coating, roll coating, curtain coating, spin coating, and knife coating, depending on the shape of a substrate and the desired state of the cured coating (e.g., coating thickness). The cured coating or film preferably has a thickness of 0.1 to 100 μm although the thickness is not particularly limited.

Although the cured coating (product) has an improved surface hardness, a functional layer (surface) may further be laid on the cured coating surface. Especially a cured film in the form of an inorganic evaporated layer may preferably be laid on the cured coating in order to impart mar resistance. The inorganic evaporated film is not particularly limited as long as it is formed by a dry film deposition method. Included are films based on at least one metal or oxide, nitride or sulfide thereof, the metal being selected from the group consisting of Si, Ti, Zn, Al, Ga, In, Ce, Bi, Sb, B, Zr, Sn and Ta. Also included are diamond-like carbon films having a high hardness and insulating properties.

The method for depositing an inorganic evaporated film is not particularly limited as long as it is a dry film deposition method. Suitable dry film deposition methods include physical gas phase growth methods such as resistance heating evaporation, EB evaporation, molecular beam epitaxy, ion beam deposition, ion plating, and sputtering, and chemical vapor deposition (CVD) methods such as thermal CVD, plasma CVD, photo CVD, epitaxial CVD, atomic layer CVD, and cat-CVD. Preferably the inorganic evaporated film has a thickness of 0.1 to 10 μm.

EXAMPLES

Examples of the invention are given below by way of illustration and not by way of limitation. All parts are by weight.

Compounds are identified by a nuclear magnetic resonance (NMR) spectrometer 400M (Bruker), unless otherwise stated. The notation of resonance magnetic field is given by using tetramethylsilane as an external standard and expressing resonance lines on a lower magnetic field side as positive values in parts per million (ppm).

(1) Synthesis of Source Compound and Organosilane Compounds for Comparative Examples Synthesis Example 1

Synthesis of 1,3,5,7-tetramethyl-1,3,5,7-tetrakis(3'-aminopropyl)-cyclotetrasiloxane-trifluoromethane-sulfonate In a porcelain evaporating dish, 1.64 g of 3-aminopropylmethyldiethoxysilane (KBE-902, Shin-Etsu Chemical Co., Ltd) was weighed. With stirring, a mixture of 1.96 g of trifluoromethanesulfonic acid (Tokyo Chemical industry Co., Ltd.) and 23.6 g of deionized water was added thereto. The mixture was stirred at room temperature for 2 hours. The evaporating dish with the reaction mixture was placed on a hot plate at 60° C. and kept in a draft, allowing volatiles to volatilize off. After reaction, the reaction mixture was washed with a chloroform/acetone (1/1=vol/vol) mixture and dried by means of a vacuum pump, yielding a white solid. From the data of $^1$H-NMR spectroscopy and comparison with Non-Patent Document 1, the product was identified to be a cyclosiloxane. FIG. 1 shows its $^1$H-NMR spectrum.

$^1$H-NMR (400 MHz, D$_2$O) δ: 3.05 (t, J=7.6 Hz, 8H), 1.85-1.75 (m, 8H), 0.80-0.70 (m, 8H), 0.28 (s, 112H)

Comparative Synthesis Example 1

Synthesis of Acrylic Functional POSS

The silsesquioxane described in Patent Document 1 was synthesized by the following procedure.

A separable flask equipped with a reflux condenser, thermometer and stirrer was charged with 142 parts of 3-acryloyloxypropyltrimethoxysilane (KBM-5103, Shin-Etsu Chemical Co., Ltd), 500 parts of isopropyl alcohol, 0.10 part of methoquinone, 1.0 part of tetrabutylammonium fluoride, and 20 parts of deionized water. The contents were reacted at 20° C. for 24 hours, obtaining a yellow clear liquid. The liquid was concentrated by vacuum distillation to a nonvolatile content of 50 wt %. Thereafter, 150 parts of ethylene glycol monobutyl ether was added. The vacuum distillation was continued, obtaining 250 parts of a solution having a nonvolatile content of 40 wt % as a colorless clear liquid.

Comparative Synthesis Example 2

Synthesis of Acrylic Functional Silane Having Urea Moiety

The organosilicon compound described in Patent Document 3 was synthesized by the following procedure.

A 1-L separable flask equipped with a stirrer, reflux condenser, dropping funnel and thermometer was charged with 179.3 g of γ-aminopropyltrimethoxysilane (KBM-903, Shin-Etsu Chemical Co., Ltd) and cooled to 0° C. in an ice bath. To the flask 141.2 g of acryloxyethyl isocyanate (Karenz AOI, Showa Denko K.K.) was added dropwise. The contents were stirred for 4 hours while heating at 30° C., obtaining an acrylic functional silane having a urea moiety as a pale yellow liquid.

(2) Synthesis of Organosilicon Compound

Example 1-1

Synthesis of Organosilicon Compound TM1

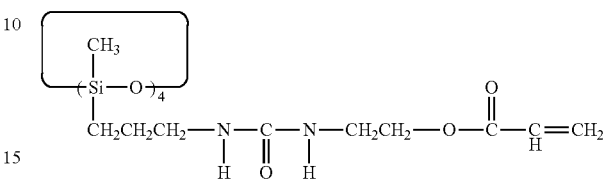

TM1

Figure 2:
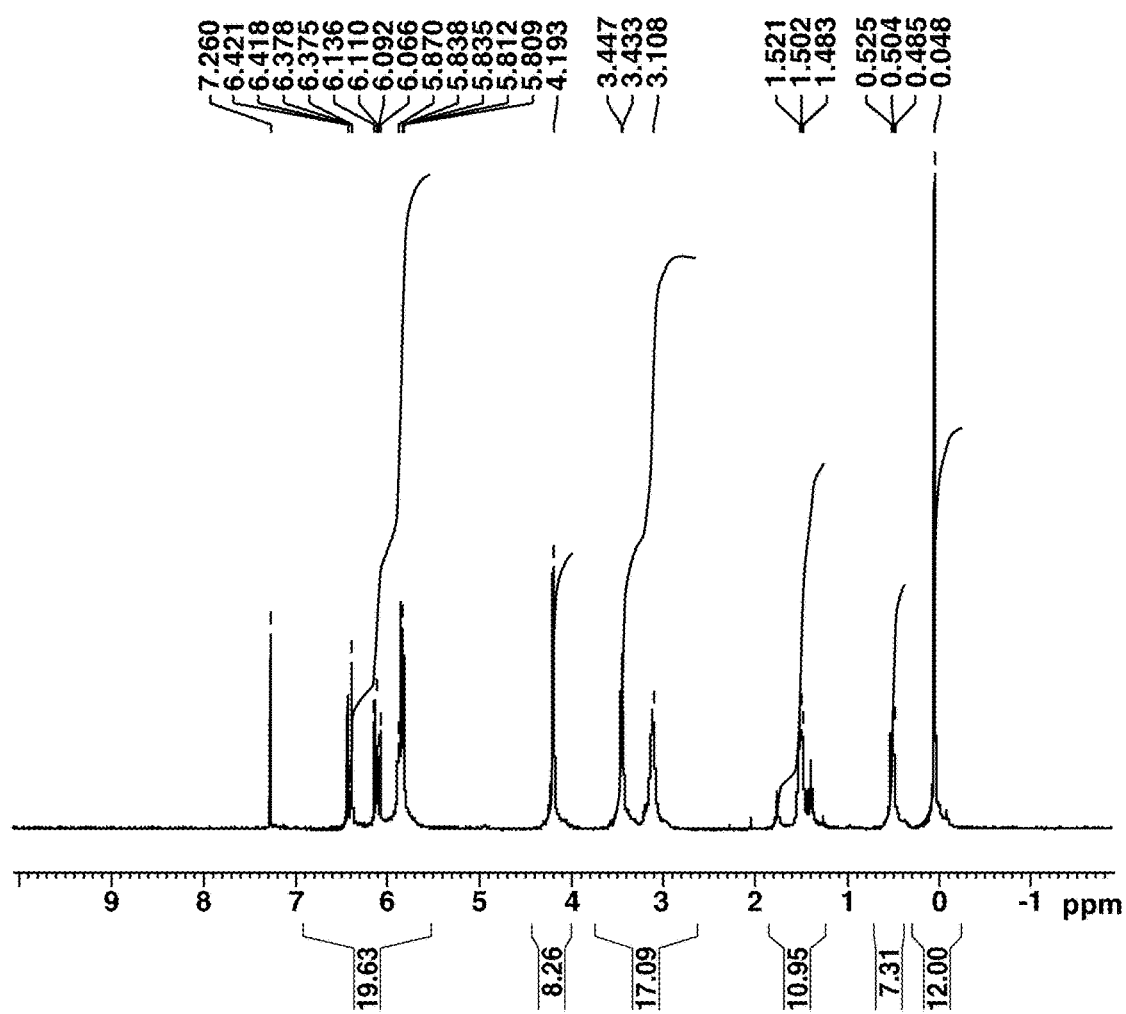
FIG. 2 is a diagram of $^1$H-NMR spectrum of the organosilicon compound obtained in Example 1-1.
Figure 3:
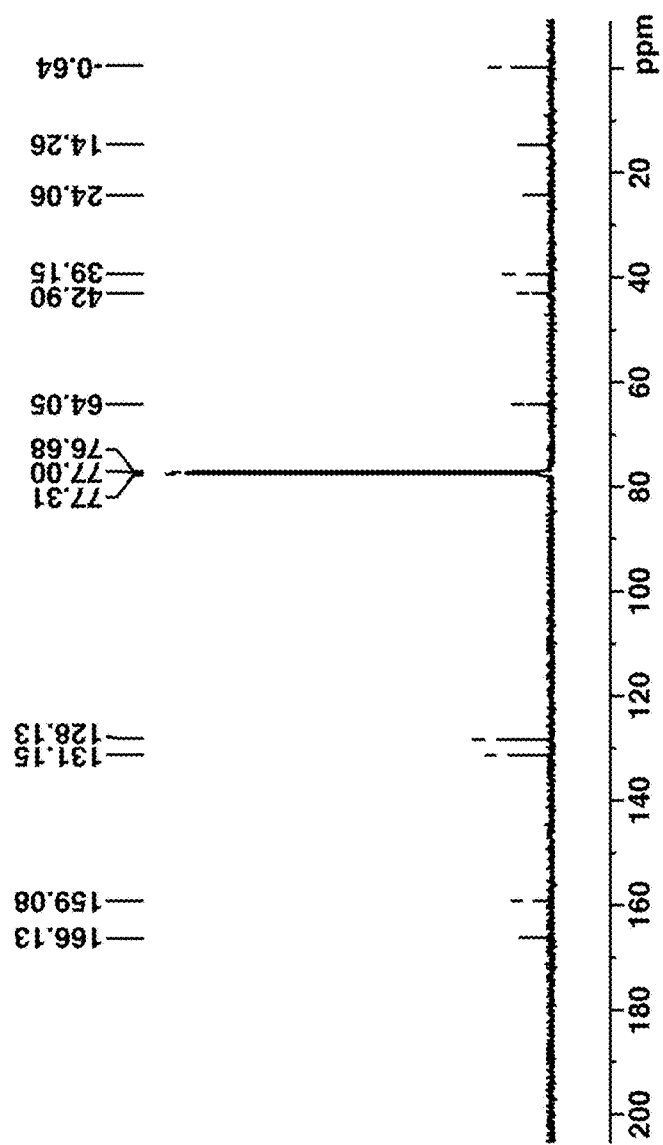
FIG. 3 is a diagram of $^{13}$C-NMR spectrum of the organosilicon compound obtained in Example 1-1.

A 30-mL recovery flask with a stirrer was charged with 0.53 g of the cyclosiloxane in Synthesis Example 1, 0.23 g of trimethylamine (Tokyo Chemical Industry Co., Ltd.), and 5 ml of tetrahydrofuran. The cyclosiloxane was kept suspended because it was substantially insoluble. With stirring, 0.29 g of 2-isocyanatoethyl acrylate (Karenz AOI, Showa Denko K.K.) was added thereto. As the suspended matter dissolved, the mixture assumed a clear and uniform appearance. Stirring was continued for 1 hour at room temperature, after which 10 ml of water and 10 ml of ethyl acetate were added. The mixture was shaken. The organic layer consisting of the ethyl acetate was separated and 3 g of anhydrous sodium sulfate was added thereto. The organic layer was filtered and stripped of volatiles by means of a vacuum pump, yielding 0.45 g of a white solid. The product was analyzed by $^1$H and $^{13}$C-NMR, finding that the cyclosiloxane was converted to a compound of structural formula TM1 while maintaining its four-membered ring conformation. FIGS. 2 and 3 show $^1$H-NMR and $^{13}$C-NMR spectra of the compound, respectively.

$^1$H-NMR (400 MHz, CDCl$_3$) δ: 6.40 (dd, J=17.6, 1.2 Hz, 4H), 6.10 (dd, J=17.6, 10.4 Hz, 4H), 5.87 (s, 4H), 5.85 (s, 4H), 5.82 (dd, J=10.4, 1.2 Hz, 4H), 4.19 (t, J=5.6 Hz, 8H), 3.44 (d, J=5.6 Hz, 8H), 3.11 (br m, 8H), 1.55-1.45 (m, 8H), 0.50-0.55 (m, 8H), 0.05 (s, 12H)

$^{13}$C-NMR (100 MHz, CDCl$_3$) δ: 166.1, 159.1, 131.2, 128.1, 64.1, 42.9, 39.2, 24.1, 14.3, −0.6

(3) Preparation of Curable Composition

Example 2-1

Preparation of Actinic Radiation-Curable Composition (2)

In a 100-mL brown plastic bottle, 9 parts of compound TM1 in Example 1-1, 1 part of 2-hydroxy-2-methyl-1-phenylpropan-1-one (IRGACURE 1173, BASF) and 40 parts of propylene glycol monomethyl ether were mixed until thoroughly dissolved, obtaining an actinic radiation-curable composition (2).

Comparative Example 2-1

Preparation of Actinic Radiation-Curable Composition (R1)

In a 100-mL brown plastic bottle, 9 parts of the silsesquioxane solution in Comparative Synthesis Example 1, 1 part of 2-hydroxy-2-methyl-1-phenylpropan-1-one and 40 parts of propylene glycol monomethyl ether were mixed until thoroughly dissolved, obtaining an actinic radiation-curable composition (R1).

Comparative Example 2-2

Preparation of Actinic Radiation-Curable Composition (R2)

In a 100-mL brown plastic bottle, 9 parts of the acrylic functional silane having a ureido moiety in Comparative Synthesis Example 2, 1 part of 2-hydroxy-2-methyl-1-phenylpropan-1-one and 40 parts of propylene glycol monomethyl ether were mixed until thoroughly dissolved, obtaining an actinic radiation-curable composition (R2).

(4) Preparation of Cured Product and Evaluation of Properties

Example 3-1

The actinic radiation-curable composition (2) in Example 2-1 was coated onto a polycarbonate resin sheet of 0.5 mm thick (Iupilon® sheet from Mitsubishi Gas Chemical Co., Inc.) and exposed to UV in a dose of 600 mJ/cm² at 80° C., obtaining a cured product.

Comparative Examples 3-1 and 3-2

Cured products were prepared as in Example 3-1 except that the actinic radiation-curable compositions (R1) and (R2) in Comparative Examples 2-1 and 2-2 were used instead of the actinic radiation-curable composition (2).

The cured products prepared in Example 3-1 and Comparative Examples 3-1 and 3-2 were evaluated for steel wool resistance, flexing property, and resistance to inorganic evaporation by the following tests. The results are summarized in Table 1.

Steel Wool Resistance

The polycarbonate resin sheet included a section having the cured product formed thereon (coated section) and a section not having the cured product formed thereon (bare section). The sheet was rubbed with steel wool #000 under a load of 100 g over 20 back-and-forth strokes. The sample was rated poor "x" when no difference was detected in mar level between the coated section and the bare section and good "○" when the coated section was little marred. FIG. 4 is a photograph showing the appearance of the cured product in Example 3-1 after the steel wool rubbing test.

Flexing Property

A flexing test was performed according to JIS K5600-5-1. The sample was rated poor "x" when it cracked and good "○" for no cracking, at a curvature of 2 mm.

Resistance to Inorganic Evaporation

According to the technique described in J. Am. Chem. Soc., 2006, 128, pp 11018, the sample was tested by feeding oxygen, argon, and tetraethoxysilane (KBE-04, Shin-Etsu Chemical Co., Ltd) as process gases in vacuum, energizing a RF coil to create a plasma, and exposing the sample to the plasma. The sample was rated poor "x" when it was whitened or otherwise degraded and good "○" when it is not degraded.

TABLE 1

|  | Example 3-1 | Comparative Example 3-1 | Comparative Example 3-2 |
|---|---|---|---|
| Steel wool resistance | ○ | ○ | X |
| Flexing property | ○ | X | X |
| Resistance to inorganic evaporation | ○ | ○ | X |

As seen from Table 1, the cured product in Example 3-1 which was obtained from the composition containing the inventive organosilicon compound was improved in all of steel wool resistance, flexing property, and resistance to inorganic evaporation. On the other hand, the cured product in Comparative Example 3-1 which was prepared using a POSS type acrylic functional polysiloxane having a similar closed ring structure showed insufficient flexing properly. The cured product in Comparative Example 3-2 which was prepared using an acrylic functional silane having a urea moiety was poor in all properties.

As demonstrated above, the inventive organosilicon compound has properties which are unexpected from a combination of past knowledges. It is presumed that the compound exhibits these properties due to its single tetramer structure. Such a correlation between properties and structure has not been reported thus far.

Japanese Patent Application No. 2016-031818 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound having the general formula (1):

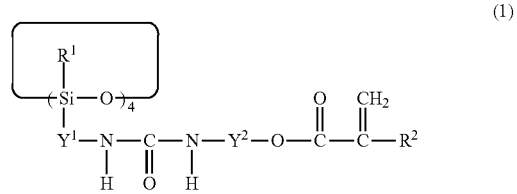

wherein $R^1$ is a $C_1$-$C_6$ alkyl group, $R^2$ is hydrogen or methyl, and $Y^1$ and $Y^2$ are each independently a $C_1$-$C_{10}$ linear alkylene group.

2. The organosilicon compound of claim 1 wherein $R^1$ is a $C_1$-$C_3$ alkyl group, $R^2$ is hydrogen, and $Y^1$ and $Y^2$ are each independently a $C_1$-$C_5$ linear alkylene group.

3. An actinic radiation-curable composition comprising the organosilicon compound of claim 1.

4. The composition of claim 3 wherein the organosilicon compound is present in an amount of at least 10% by weight.

5. The composition of claim 4, which comprises at least one of the following components:
   a polymerizable vinyl monomer;
   an inorganic oxide filler;
   a photoinitiator;
   a solvent.

6. The composition of claim 5, which comprises a polymerizable vinyl monomer.

7. The composition of claim 6, wherein said polymerizable vinyl monomer is present in an amount of 10 to 90% by weight.

8. The composition of claim 7, wherein said polymerizable vinyl monomer is present in an amount of 20 to 90% by weight.

9. The composition of claim 5, which comprises a photoinitiator.

10. The composition of claim 5, which comprises an inorganic oxide filler.

11. The composition of claim 10, wherein the inorganic oxide filler is present in an amount of 1 to 30% by weight.

12. The composition of claim 11, wherein the inorganic oxide filler is present in an amount of 5 to 20% by weight.

13. The composition of claim 5, which comprises a solvent.

14. The composition of claim 13, which comprises 10 to 90% by weight of solvent.

15. The composition of claim 14, which comprises 20 to 60% by weight of solvent.

16. The composition of claim 5, which has a solids content of 1 to 50% by weight.

17. The composition of claim 16, which has a solids content of 5 to 30% by weight.

18. The composition of claim 17, which has a solids content of 10 to 30% by weight.

* * * * *